United States Patent [19]

Nishiyama et al.

[11] 4,344,951
[45] * Aug. 17, 1982

[54] N-BENZOYL N'-PYRIDYLOXY PHENYL UREA

[75] Inventors: Ryuzo Nishiyama, Takatsuki; Takahiro Haga, Kusatsu; Tadaaki Toki; Tohru Koyanagi, both of Moriyama; Shigeo Murai, Yookaichi, all of Japan

[73] Assignee: Ishihara Sangyo Kaisha Ltd., Osaka, Japan

[*] Notice: The portion of the term of this patent subsequent to Jan. 12, 1999, has been disclaimed.

[21] Appl. No.: 250,077

[22] Filed: Apr. 1, 1981

Related U.S. Application Data

[63] Continuation-in-part of Ser. No. 183,650, Sep. 3, 1980, Pat. No. 4,310,530.

[30] Foreign Application Priority Data

Sep. 7, 1979 [JP] Japan ................................ 54-114862
Feb. 8, 1980 [JP] Japan .................................. 55-14430

[51] Int. Cl.³ .................... C07D 213/64; A01N 43/40
[52] U.S. Cl. ..................................... 424/263; 546/291
[58] Field of Search ........................ 546/291; 424/263

[56] References Cited

U.S. PATENT DOCUMENTS 3,748,356  7/1973  Wellenga et al. ..................... 564/44
3,931,201  1/1976  Johnston ............................. 546/291
4,173,637  11/1979  Nishiyama et al. ................. 424/263
4,173,638  11/1979  Nishiyama et al. ................. 424/263

Primary Examiner—Alan L. Rotman
Attorney, Agent, or Firm—Oblon, Fisher, Spivak, McClelland & Maier

[57] ABSTRACT

N-benzoyl N'-pyridyloxy phenyl ureas having the formula

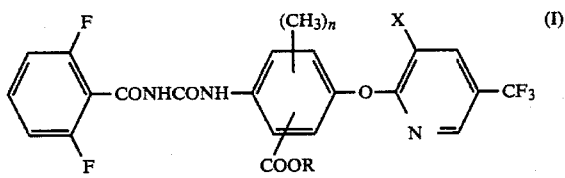

wherein X represents a halogen atom; R represents a $C_1$-$C_4$ alkyl group and n is 0, 1 or 2 are useful as insecticides.

3 Claims, No Drawings

N-BENZOYL N'-PYRIDYLOXY PHENYL UREA

This application is a continuation-in-part of parent application Ser. No. 183,650, filed Sept. 3, 1980, now U.S. Pat. No. 4,310,530.

BACKGROUND OF THE INVENTION

1. Field of the Invention

The present invention relates to novel N-benzoyl N'-pyridyloxy phenyl ureas and the process for producing the same and the insecticidal composition containing the same.

2. Description of the Prior Arts

Almost of the conventional insecticides impart neurotoxicity and contact toxicity to all kinds of insects.

It has been required to find selective insecticidal compounds without toxicity to useful insects, N-benzoyl N'-phenyl ureas disclosed in U.S. Pat. No. 3,748,356 and N-benzoyl N'-pyridyloxy phenyl ureas disclosed in U.S. Pat. No. 4,173,637 and U.S. Pat. No. 4,173,638 have such insecticidal properties.

The N-benzoyl N'-pyridyloxy phenyl ureas according to the present invention have a substantially better action than the above described known compounds.

SUMMARY OF THE INVENTION

It is an object of the present invention to provide novel N-benzoyl N'-pyridyloxy phenyl ureas.

It is another object of the present invention to provide a process for producing N-benzoyl N'-pyridyloxy phenyl ureas.

It is the other objects of the present invention to provide selective insecticidal compositions which are remarkably effective to certain injurious insects without affecting useful insects in remarkably low toxicity to animals.

The novel compounds of the present invention are N-benzoyl N'-pyridyloxy phenyl ureas having the formula

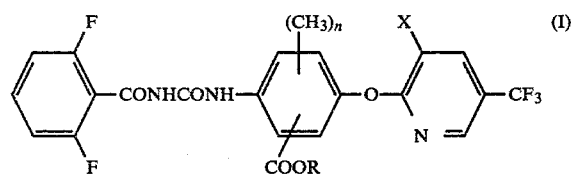

wherein X represents a halogen atom; R represents a $C_1$–$C_4$ alkyl group and n is 0, 1 or 2.

DETAILED DESCRIPTION OF THE PREFERRED EMBODIMENTS

The present invention is to provide novel N-benzoyl N'-pyridyloxy phenyl ureas having the formula

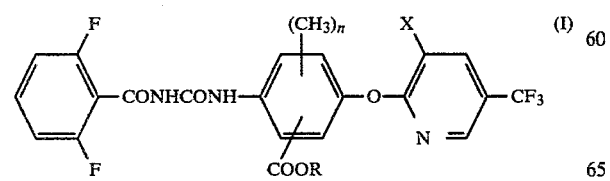

wherein X represents a halogen atom; R represents a $C_1$–$C_4$ alkyl group and n is 0, 1 or 2.

The N-benzoyl N'-pyridyloxy phenyl ureas having the formula (I) are produced by reacting a compound having the formula

wherein $R_1$ represents amino or isocyanate group with a compound having the formula

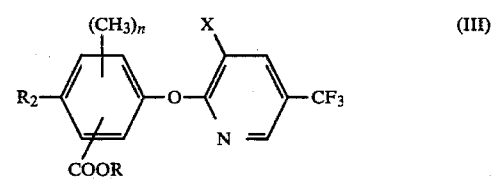

wherein $R_2$ represents an amino or isocyanate group and $R_2$ is amino group in the case that $R_1$ is isocyanate group and $R_2$ is isocyanate group in the case that $R_1$ is amino group.

More particularly, the compounds having the formula (I) can be produced by the following processes (1) and (2).

(1) The reaction of benzoyl isocyanate having the formula

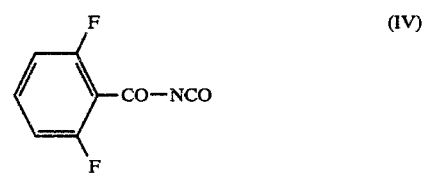

with pyridyloxy aniline having the formula

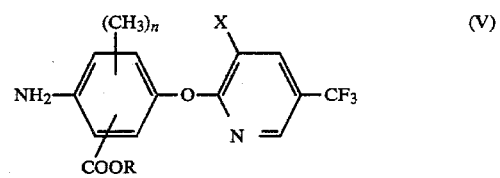

at 0° to 120° C.

(2) The reaction of benzamide having the formula

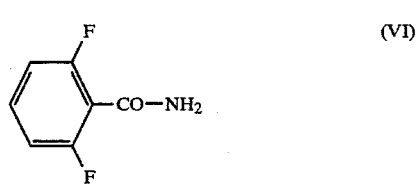

with pyridyloxy phenyl isocyanate having the formula

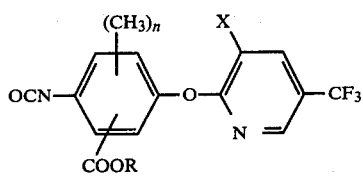
(VII)

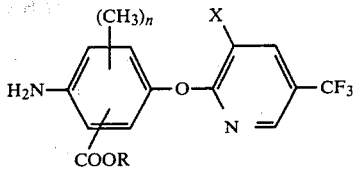

at 50° C. to refluxing temperature.

The reaction is preferably carried out in the presence of a solvent. Suitable solvents include benzene, toluene, xylene, pyridine dioxane, dimethylsulfoxide, monochlorobenzene, ethyl acetate and tetrahydrofuran.

The reaction time is usually in a range of 0.1 to 24 hours. The reaction is preferably carried out at the temperature from 50° C. to a refluxing temperature for 1 to 5 hours.

The aniline compounds having the formula (V)

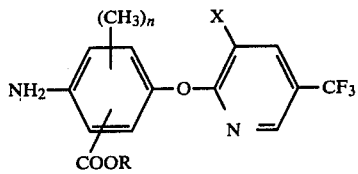

can be produced by reacting a compound having the formula

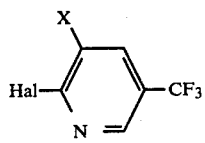

with a compound having the formula

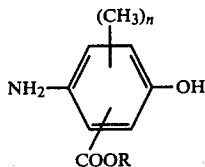

in a solvent in the presence of a base at 70° to 150° C. for 0.5 to 10 hours.

Suitable solvents can be aprotic polar solvents such as dimethylsulfoxide, dimethylformamide and hexamethylphosphoroamide; and ketones such as acetone, methyl ethyl ketone and methyl isobutyl ketone.

Suitable bases can be sodium hydroxide, potassium hydroxide, sodium carbonate and potassium carbonate.

The pyridyloxy phenyl isocyanates having the formula (VII)

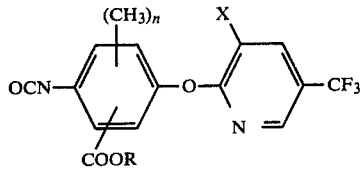

can be produced by reacting a compound having the formula with a compound having the formula COCl$_2$ in a solvent at 50° to 150° C. for 0.1 to 24 hours.

Suitable solvents can be solvents inert to phosgene such as toluene, xylene, monochlorobenzene, ethyl acetate or dioxane.

The condensation reaction is preferably carried out in nitrogen atmosphere.

It is possible to react a 2,3-dihalo-5-trifluoromethylpyridine with a phenol in the similar condition to that of the production of the aniline compound to obtain 3-halo-5-trifluoromethyl-2-pyridylphenyl ether compound and it is converted to the aniline compound by the conventional nitration and a reduction.

Certain examples of preparations of the compounds of the present invention will be described.

EXAMPLE 1

Preparation of N-(2,6-difluorobenzoyl)-N'-[3-methoxycarbonyl-4-(3-chloro-5-trifluoromethyl-2-pyridyloxy)-5-methylphenyl]urea:

Into a flask, 4.6 g. of methyl 2-hydroxy-3-methyl-5-aminobenzoate, 0.3 g. of potassium carbonate and 50 ml. of dimethylsulfoxide were charged. Nitrogen gas was fed into the flask and the charged materials were maintains out at 90° C. for 1 hour. The maintained materials were cooled at 70° C., then 5.4 g. of 2,3-dichloro-5-trifluoromethylpyridine was dropped and the reaction was carried out at 90° C. for 2 hours. After the reaction, the reaction mixture was cooled and poured into water. The product was extracted with methylene chloride. The extracted layer was washed with water and dehydrated over anhydrous sodium sulfate and methylene chloride was distilled off. The product was purified by a column chromatography with a silica gel column (hexane and ethyl acetate of 3:1) to obtain 2.5 g. of methyl 2-(3-chloro-5-trifluoromethyl-2-pyridyloxy)-3-methyl-5-aminobenzoate.

Into 20 ml. of dioxane, 2.1 g. of the resulting methyl 2-(3-chloro-5-trifluoromethyl-2-pyridyloxy)-3-methyl-5-aminobenzoate was dissolved and 1.1 g. of 2,6-difluorobenzoyl isocyanate dissolved in 5 ml. of dioxane was added dropwise and the reaction was carried out at a room temperature for 1 hour. The reaction mixture was poured into water and the resulting precipitate was filtered to obtain 2.8 g. of N-(2,6-difluorobenzoyl)-N'-[3-methoxycarbonyl-4-(3-chloro-5-trifluoromethyl-2-pyridyloxy)-5-methylphenyl]urea having m.p. of 202°–204° C.

EXAMPLE 2

Preparation of N-(2,6-difluorobenzoyl)-N'-[3-ethoxy-carbonyl-4-(3-chloro-5-trifluoromethyl-2-pyridyloxy)phenyl]urea.

A solution of 1.7 g. of 2,6-difluorobenzamide in 50 cc of dichloroethane was heated to 50° C. and 4.2 g. of oxalyl chloride was added dropwise with stirring and the reaction was continued for 1 hour with stirring to obtain 2,6-difluorobenzoyl isocyanate. Then, dichloroethane and excess of oxalyl chloride were distilled off under a reduced pressure. The residue was admixed with 50 cc of dioxane and a solution of 3.3 g. of 3-ethoxycarbonyl-4-(3-chloro-5-trifluoromethyl-2-pyridyloxy) aniline in dioxane was added dropwise and the reaction was continued for 2 hours with stirring. After the reaction, the reaction mixture was poured into water and the resulting crystal was filtered and washed with water and dried to obtain 4.8 g. of the object compound having a melting point of 183°–186° C.

The following typical compounds of the present invention were prepared by one of the processes of Example 1 using the corresponding starting materials. Typical compounds of the present invention having the formula I are as follows.

| Compound No. 1: | N-(2,6-difluorobenzoyl)-N'-[3-methoxycarbonyl-4-(3-chloro-5-trifluoromethyl-2-pyridyloxy)-5-methylphenyl]urea m.p.: 202–204° C. |
|---|---|
| Compound No. 2: | N-(2,6-difluorobenzoyl)-N'-[3-methoxycarbonyl-4-(3-chloro-5-trifluoromethyl-2-pyridyloxy)-6-methylphenyl]urea m.p.:½–176° C. |
| Compound No. 3: | N-(2,6-difluorobenzoyl)-N'-[3-ethoxycarbonyl-4-(3-chloro-5-trifluoromethyl-2-pyridyloxy)phenyl]urea m.p.: 183–186° C. |
| Compound No. 4: | N-(2,6-difluorobenzoyl)-N'-[3-ethoxycarbonyl-4-(3-bromo-5-trifluoromethyl-2-pyridyloxy)phenyl]urea m.p.: 193–196° C. |

The compounds of the present invention impart excellent selective insecticidal effect as clearly understood from the following experiments.

The compounds of the present invention impart remarkable insecticidal effect to larvae of Lepidoptera, Coleoptera, Hymenoptera and Diptera, for example, larvae of the following insects:

diamondback moth (*Plutella xylostella*), common white (*Pieris rapae crucivora*), cabbage armyworm (*Mamesta brassicae*), cabbage looper (*Plusia nigrisigma*), tobacco cutworm (*Spodoptera litura*), smaller citrus dog (*Papilio xuthus*), small blackish cochlid (*Seopelodes contracta*), fall webworm (*Hyphantria cunea*), gypsy moth (*Lymantria dispar*), rice stem borer (*Chilo suppressalis*), bollworm (*Heliothis zea*), tobacco budworm (*Heliothis virescens*), bollweevil (*Anthonomus grandis*), confused flour beetle (*Tribolium confusum*), colorado potato beetle (*Leptinotarsa decemlineata*), sawfly (*Neurotoma irdescens*), house mosquito (*Culex pipiens pallens*), house fly (*Musca domestica*).

The compounds of the present invention impart low toxicity to animals.

When the compounds are used as active ingredients of the insecticidal composition, it is possible to prepare various forms of the compositions such as dust, wettable powder, emulsifiable concentrate, invert emulsion, oil solution, aerosol preparation, etc. with adjuvants as the cases of agricultural compositions. The compositions can be applied with or without diluting them in suitable concentrations.

The insecticidal composition is usually formulated by combining 0.5 to 80 wt. % preferably 10 to 50 wt. % of an active ingredient; 5 to 99.5 wt. %, preferably 35 to 85 wt. % of a diluent; and 0 to 20 wt. % preferably 5 to 15 wt. % of the other adjuvant.

Suitable adjuvants include powdery carriers such as talc, kaolin, bentonite, diatomaceous earth, silicon dioxide, clay and starch; liquid diluents such as water, xylene, toluene, dimethylsulfoxide, dimethyl formamide, acetonitrile, and alcohol; emulsifiers, dispersing agents, spreaders etc.

The concentration of the active ingredient in the selective insecticidal composition is usually 5 to 80 wt. % in the case of the oily concentrate; and 0.5 to 30 wt. % in the case of dust; 5 to 60 wt. % in the case of wettable powder or an emulsifiable concentrate.

It is also possible to combine with the other agricultural ingredients such as the other insecticides, miticides, plant growth regulators. Sometimes synergetic effects are found.

The selective insecticides of the present invention are effective for inhibiting various injurious insects and they are usually applied at a concentration of the active ingredients of 1 to 10,000 ppm preferably 20 to 2,000 ppm.

It is possible to prevent incubation and growth of notorious insects on excrement by feeding a feed incorporating the active ingredient of the invention.

It is possible to prevent notorious insects live in water by applying the active ingredient of the present invention at said concentration and accordingly, the concentration in water can be lower than said range in water.

EXPERIMENT 1

Each active ingredient was dispersed in water to prepare each dispersion of a concentration of 400, 200, 100 and 50 ppm. Leaves of cabbage were dipped into each dispersion for about 10 seconds and taken out and dried under passing air.

A piece of moistened filter paper was put on each Petri dish (diameter 9 cm) and the dried leaves of cabbage were put on the filter paper and larvae of diamondback moth in 2nd or 3rd instar were fed on them and the Petri dishes were covered and kept in constant temperature at 28° C. with lightening. After 8 days from the treatment with the dispersion, the mortal larvea were measured and the mortality rates were calculated by the following equation:

$$\text{Mortality rate} = \frac{\text{Mortal larvae}}{\text{total larvae}} \times 100$$

The results are shown in Table 1.

TABLE 1

| Active ingredient | Mortality rate (%) | | | |
|---|---|---|---|---|
| | 400 ppm | 200 ppm | 100 ppm | 50 ppm |
| Compound No. 1 | 100 | 100 | 100 | 100 |
| Compound No. 2 | 100 | 100 | 100 | 100 |
| Compound No. 3 | 100 | 100 | 100 | 90 |
| Compound No. 4 | 100 | 100 | 100 | 100 |

EXPERIMENT 2

In accordance with the method of Experiment 1 except using tabacco cutworm (*Spodoptera litura*) in 2nd or 3rd instar instead of diamondback moth in 2nd or 3rd instar, the tests were carried out, using a dispersion of a concentration of 400 ppm. The results are shown in Table 2.

TABLE 2

| Active ingredient | Mortality rate (%) |
| --- | --- |
| Compound No. 1 | 100 |
| Compound No. 2 | 100 |
| Compound No. 3 | 100 |
| Compound No. 4 | 100 |

EXPERIMENT 3

Each composition of powdery feed (manufactured by Oriental Enzyme Co.), wheat bran and a solution of each active ingredient at a specific concentration at a ratios of 1:1:2 by weight as a medium for larvae of housefly was put into each cup. Houseflies in 2nd or 3rd instar were put in the cup and the cup was covered with gauze. After 12 days, mortal larvae were measured and the mortality rates were calculated by the equation of Experiment 1. The results are shown in Table 3.

TABLE 3

| Active ingredient | Mortality rate (%) | | | | | |
| --- | --- | --- | --- | --- | --- | --- |
| | 80 ppm | 40 ppm | 20 ppm | 10 ppm | 5 ppm | 2.5 ppm |
| Comp. No. 1 | 100 | 100 | 100 | 100 | 100 | 100 |
| Comp. No. 2 | 100 | 100 | 100 | 100 | 100 | 100 |
| Comp. No. 3 | 100 | 100 | 100 | 100 | 95 | 85 |
| Comp. No. 4 | 100 | 100 | 100 | 100 | 95 | 85 |

EXPERIMENT 4

Into a deep Petri dish (diameter of 9 cm), about 250 ml. of each dispersion of each active ingredient having concentration of 100 ppb was charged and striped mosquitos in 3rd instar were put and the Petri dish was covered and kept in a constant temperature bath at 28° C. with light. After 10 days, the mortal larvae were measured and the mortality rates were calculated by the equation of Experment 1. The results are shown in Table 4.

TABLE 4

| Active ingredient | Mortality rate (%) |
| --- | --- |
| Compound No. 1 | 100 |
| Compound No. 2 | 100 |
| Compound No. 3 | 100 |
| Compound No. 4 | 100 |

| Composition 1: | |
| --- | --- |
| Active ingredient | 20 wt. parts |
| N,N-dimethylformamide | 70 wt. parts |
| Polyoxyethylenealkylphenyl ether | 10 wt. parts |

The components were uniformly blended to dissolve the active ingredient to prepare an emulsifiable concentrate.

| Composition 2: | |
| --- | --- |
| Active ingredient | 5 wt. parts |
| Talc | 95 wt. parts |

The mixture was pulverized to uniformly mix them to prepare a dust.

| Composition 3: | |
| --- | --- |
| Active ingredient | 50 wt. parts |
| Fine silica | 15 wt. parts |
| Fine clay | 25 wt. parts |
| Sodium naphthalenesulfonate-formaldehyde condensate | 2 wt. parts |
| Dialkylsulfosuccinate | 3 wt. parts |
| Polyoxyethylenealkylaryl ether sulfate | 5 wt. parts |

The mixture was pulverized to uniformly mix them to prepare a wettable powder.

We claim:

1. N-benzoyl N'-pyridyloxy phenyl ureas having the formula

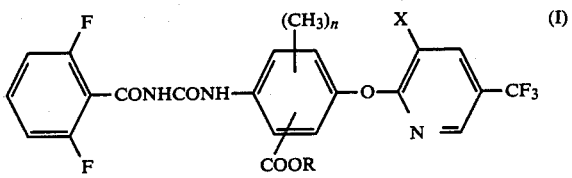

wherein X represents a halogen atom; R represents a $C_1$-$C_4$ alkyl group and n is 0, 1 or 2.

2. N-(2,6-difluorobenzoyl)-N'-[3-methoxycarbonyl-4-(3-chloro-5-trifluoromethyl-2-pyridyloxy)-5-methylphenyl]urea; N-(2,6-difluorobenzoyl)-N'-[3-methoxycarbonyl-4-(3-chloro-5-trifluoromethyl-2-pyridyloxy)-6-methylphenyl]urea; N-(2,6-difluorobenzoyl)-N'-[3-ethoxycarbonyl-4-(3-chloro-5-trifluoromethyl-2-pyridyloxy)phenyl]urea; and N-(2,6-difluorobenzoyl)-N'-[3-ethoxycarbonyl-4-(3-bromo-5-trifluoromethyl-2-pyridyloxy)phenyl]urea.

3. An insecticidal composition comprising an effective amount of a N-benzoyl N'-pyridyloxy phenyl urea having the formula (I) according to claim 1 as an active ingredient together with an inert carrier or diluent.

* * * * *